United States Patent [19]

Chan

[11] 4,036,960
[45] July 19, 1977

[54] 1,3-BENZOXAZIN-4-ONE DERIVATIVES AND THEIR USE AS OVICIDES

[75] Inventor: David Cheong King Chan, San Francisco, Calif.

[73] Assignee: Chevron Research Company, San Francisco, Calif.

[21] Appl. No.: 645,000

[22] Filed: Dec. 29, 1975

[51] Int. Cl.² .......................... A01N 9/00; A01N 9/22; C07D 265/00; C07D 273/00
[52] U.S. Cl. .............................. 424/248.5; 260/244 R
[58] Field of Search ........... 260/244; 424/248, 248.51, 424/248.5

[56] References Cited

U.S. PATENT DOCUMENTS

| | | | |
|---|---|---|---|
| 3,542,774 | 11/1970 | Shavel et al. | 260/244 R |
| 3,743,641 | 7/1973 | Makula et al. | 260/244 R |
| 3,880,847 | 4/1975 | Böshagen | 260/244 R |

OTHER PUBLICATIONS

Chem. Abst. 59, 2806(e) (1963)-Kurihara et al., "4-Oxo-2,3dihydro-5,6-benz-1,3-oxazine derivatives".

Primary Examiner—Albert T. Meyers
Assistant Examiner—D. W. Robinson
Attorney, Agent, or Firm—J. A. Buchanan, Jr.; Dix A. Newell; T. G. DeJonghe

[57] ABSTRACT

Compounds of the formula

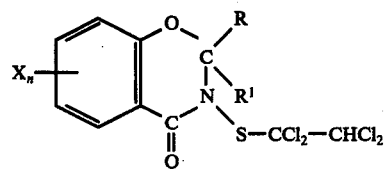

wherein X is halogen of atomic number 9 through 35, i.e., fluorine, chlorine or bromine, or alkyl of 1 to 3 carbon atoms, $n$ is 0, 1 or 2, and R and R¹ are individually hydrogen, methyl or ethyl, possess acarid ovicidal activity.

7 Claims, No Drawings

1,3-BENZOXAZIN-4-ONE DERIVATIVES AND THEIR USE AS OVICIDES

BACKGROUND OF THE INVENTION

1. Field of the Invention

The present invention is directed to tetrachloroethylthio-substituted 1,3-benzoxazin-4-ones and their use as ovicides.

2. Prior Art

U.S. Pat. No. 2,943,087 discloses derivatives of 4-oxo-2,3-dihydro(benz-1,3-cxazines) and their usefulness for analgesic, antipyretic and antiphlogistic properties in animals as well as humans. For example, 4-oxy-2-(beta-chloroethyl)-2,3-dihydro(benz-1,3-cxazine), or in the nomenclature used in this specification, 2-(beta-chloroethyl)-1,3-benzoxazin-4-one), is disclosed.

U.S. Pat. No. 3,257,396 discloses certain heterocyclic 1,3-benzoxazinone derivatives possessing pharmacological properties.

U.S. Pat. No. 3,459,748 discloses hydroxyalkylene-substituted benzoxazines and benzothiazines, and their utility as therapeutic substances and antibacterial substances.

Tohoku Yakka Daigaku Kigs 9, 69–76 (1962) (C.A. 59:2806e) discloses various benz-1,3-oxazine derivatives as analgesics and antipyretics.

DESCRIPTION OF THE INVENTION

The 1,3-benzoxazin-4-ones of the present invention represented by the formula

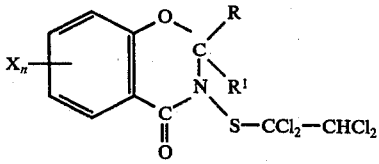

wherein X is halogen of atomic number 9 through 35, i.e., fluorine, chlorine or bromine, or alkyl of 1 to 3 carbon atoms, $n$ is 0, 1 or 2, and R and $R^1$ are individually hydrogen, methyl or ethyl, possess acarid ovicidal activity.

Preferably X is chlorine or methyl, more preferably chlorine; $n$ is preferably 0 or 1 and more preferably 0.

Preferably R and $R^1$ individually are hydrogen or methyl. The most preferred compounds have one of R and $R^1$ as hydrogen and the other as methyl.

Representative compounds of the present invention include:

3-(1',1',2',2'-tetrachloroethylthio)-1,3-benzoxazin-4-one
2,2-dimethyl-3-(1',1',2',2'-tetrachloroethylthio)-1,3-benzoxazin-4-one
2-methyl-3-(1',1',2',2'-tetrachloroethylthio)-1,3-benzoxazin-4-one
2-ethyl-3-(1',1',2',2'-tetrachloroethylthio-1,3-benzoxazin-4-one
2,2-diethyl-3-(1',1',2',2'-tetrachloroethylthio)-1,3-benzoxazin-4-one
2,2-dimethyl-3-(1',1',2',2'-tetrachloroethylthio)-7-chloro-1,3-benzoxazin-4-one
2,2-dimethyl-3-(1',1',2',2'-tetrachloroethylthio-7,8-dichloro-1,3-benzoxazin-4-one
2,2-diethyl-3-(1',1',2',2'-tetrachloroethylthio)-5-fluoro-1,3-benzoxazin-4-one
2,2-dimethyl-3-(1',1',2',2'-tetrachloroethylthio)-5-bromo-1,3-benzoxazin-4-one
2,2-dimethyl-3-(1',1',2',2'-tetrachloroethylthio)-5-chloro-6-methyl-1,3-benzoxazin-4-one
2-methyl-3-(1',1',2',2'-tetrachloroethylthio)-6-n-propyl-1,3-benzoxazin-4-one
3-(1',1',2',2'-tetrachloroethylthio)-6,7-diethyl-1,3-benzoxazin-4-one

METHOD OF PREPARATION

The compounds of this invention are prepared by a two-step synthesis starting from an appropriately substituted salicylamide. The first step involves condensation with an aldehyde or ketone, e.g.:

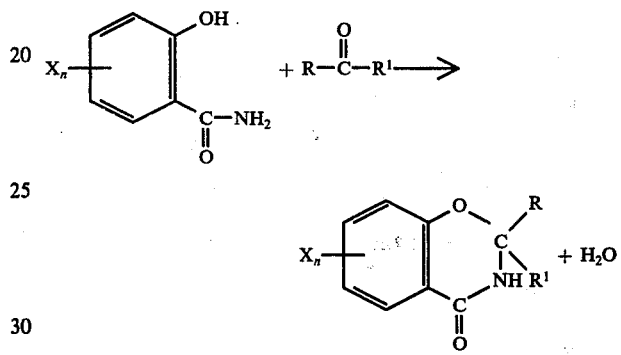

and the second step is a sulfenylation reaction with tetrachloroethylsulfenyl halide, e.g.:

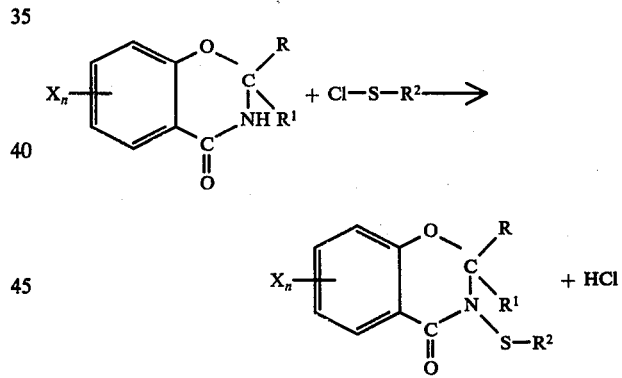

wherein X, N, R and $R^1$ have the same meaning as stated before, and $R^2$ is tetrachloroethyl.

Salicylamide can be purchased or is readily prepared by reaction of salicylic acid with ammonia. Carbonyl compounds, such as aldehydes and ketones, are also available in commercial quantities.

The reaction charge comprises 1 mol of a salicylamide and from 1 to 3 mols of the carbonyl compound. The reaction is carried out in a solvent having a boiling point in excess of 50° C. Typical solvents include chloroform, benzene, tetrahydrofuran, and the like. Sufficient solvent is used to dissolve the two reactants, preferably from 2 to 10 volumes of solvent per volume of reactants. The reaction is acid-catalyzed; useful catalyst include the sulfonic acids such as toluene sulfonic acid; acidic ion-exchange resins such as the Amberlite type; also, sulfuric acid, boron trifluoride etherate and trichloroacetic acid may be used. Only small quantities of catalyst are required, usually in the range of 2 to 20% by weight based on the salicylamide compound. The reaction is carried out at the boiling point of the solvent, i.e., from 50° to 150° C. Superior yields are obtained by adding a dehydrating agent to absorb the water formed as a by-product. Molecular sieves are the preferred dehydrating agent, but calcium chloride or other agent may also be used. Azeotropic removal of water during reaction gives very inferior results. The course of reaction is followed by measuring the disappearance of salicylamide. This measurement is preferably done by thin-layer chromatography, although other analytical procedures may be used. Reaction is continued until essentially all of the salicylamide has reacted, about 1 to 48 hours.

The crude reaction product is washed with dilute caustic and water, and after drying the solvent is removed by distillation, preferably under vacuum. This material may be used as is for the next step, or it may be purified by recrystallization from a suitable solvent, such as a benzene-hexane mixture.

The second step of the synthesis is carried out by reacting the 1,3-benzoxazin-4-one prepared as described above with an equal molar amount of polyhaloalkylsulfenyl chloride. The reaction is carried out in a solvent such as dichloromethane, ethyl acetate, ethyl ether, benzene, etc. The quantity of solvent should be sufficient to dissolve the reactants and may vary from 5 to 20 volumes of solvent per volume of reactants. A basic material is added to the reaction mixture to capture the by-product hydrogen chloride. Suitable bases include pyridine, triethylamine, triethylene diamine, etc. At least one equivalent amount of base per mol of sulfenyl chloride is needed. The reaction is carried out at temperatures in the range 0° to 25° C. The extent of reaction is determined by observing the disappearance of the amide hydrogen by nuclear magnetic resonance (NMR) analysis. The reaction is continued until essentially all of this hydrogen has disappeared, usually from 0.5 to 24 hours.

The crude reaction mixture is first washed with water, then dried, and finally treated under vacuum to remove the solvent. This crude product may be purified by chromatography, or by crystallization from a suitable solvent.

The present invention will be more fully understood by reference to the following examples, which illustrate a method of preparation of the novel compounds of the present invention. The examples are in no way intended to limit the invention described herein. Unless otherwise indicated, percentages are by weight.

EXAMPLES

Example 1

Preparation of 2,2-dimethyl-1,3-benzoxazin-4-one

A 500-ml flask was charged with 250 ml of chloroform, 27.4 g (0.2 mol) of salicylamide, 23.2 g (0.4 mol) of acetone and 2.7 g of toluene sulfonic acid monohydrate. The flask was equipped with a Soxhlet extraction vessel containing 36.7 g of molecular sieves (Linde Type 3A, 1/16 inch) in the thimble. The reaction mixture was refluxed for 24 hours. Then fresh sieves were placed in the Soxhlet and 10 g of acetone was added to the reaction mixture. Reflux was continued for 24 hours.

After cooling, the crude reaction mixture was washed with 100 ml of 5% caustic, and then with 200 ml of water. The chloroform solution was dried over $MgSO_4$ and then the solvent was removed under vacuum to give 34.6 g of product. Analysis, calculated for $C_{10}H_{11}NO_2$: %C, 67.78; %H, 6.26; %N, 7.90. Found: %C, 68.2, %H, 6.1; %N, 8.7. The melting point was 139°–140° C.

Example 2

Preparation of 2,2-dimethyl-3-(1',1',2',2'-tetrachloroethylthio)-1,3-benzoxazin-4-one A 250-ml flask equipped with condenser, stirrer and thermometer and immersed in an ice bath was charged with 150 ml of dichloromethane, 8.3 g (0.047 mol) of 2,2-dimethyl-1,3-benzoxazin-4-one and 10.9 g (0.047 mol) of 1,1,2,2-tetrachloroethylsulfenyl chloride. Then 4.75 g (0.047 mol) of triethylamine dissolved in 10 ml of dichloromethane was added dropwise over a period of 15 minutes. The resulting solution was stirred at 0° C for 45 more minutes. The crude reaction mixture was washed three times with equal quantities of water. The organic phase was dried and then stripped of solvent. The resulting residue was washed with 200 ml of hexane and filtered. The dried filter cake, 5.1 g, was unreacted 2,2-dimethyl-1,3-benzoxazin-4-one. The filtrate was stripped of hexane and the resulting residue was chromatographed through 300 g of silica gel using 1 liter of hexane, 1 liter of 3% ether-hexane and 3 liters of 5% ether-hexane to give 2.8 g of 2,2-dimethyl-3-(1',1',2',2'-tetrachloroethylthio)-1,3-benzoxazin-4-one. Analysis, calculated for $C_{12}H_{11}Cl_4NO_2S$: %C, 37.81; %S, 8.55. Found: %Cl, 40.0; %S, 8.8. NMR spectra confirmed the assigned structure. The infrared spectra had strong adsorption at 1785, 1600, 1460, 1300, 1240 and 740 $cm^{-1}$. These spectra also had many distinct, medium-strength adsorption bands in the 800–1700 $cm^{-1}$ region.

Other compounds were prepared by the same general procedures as in the above examples. These compounds are listed in Table I.

TABLE I

| Example No. | Compound | Melting Point ° C | Elemental Analysis | | | |
| --- | --- | --- | --- | --- | --- | --- |
| | | | S Calc | Cl Calc | S Found | Cl Found |
| 3 | 2-ethyl-3-(1',1',2',2'-tetrachloroethylthio)-1,3-benzoxazine-4-one | oil | 8.6 | 37.8 | 9.6 | 39.6 |
| 4 | 2-methyl-3-(1',1',2',2'-tetrachloroethylthio)-1,3-benzoxazine-4-one | 98–100 | 8.9 | 39.3 | 9.0 | 39.2 |
| 5 | 2,2-dimethyl-3-(trichloromethylthio)-1,3-benzoxazine-4-one | 72–74 | 9.8 | 32.6 | 9.8 | 31.7 |
| 6 | 2-isopropyl-3-(1',1',2',2'-tetrachloroethylthio)-1,3-benzoxazine-4-one | oil | 8.2 | 36.4 | 9.5 | 36.2 |

UTILITY

The compounds of the present invention exhibit ovicidal activity, particularly acarid ovicidal activity, as shown in the following example.

EXAMPLE A

To test ovicidal activity, pinto bean leaves having two-spotted mite (*Tetranychus telarius* L.) eggs attached thereto were dipped into an alcohol-water solution of the candidate toxicant containing a small amount of nonionic emulsifier. The toxicant concentration was 40 ppm. The leaves were dried, and then held at 85° F for about 7 days. The dead eggs were then counted and the percent control determined. The results are reported in Table II.

TABLE II

| Compound | Two-spotted mite eggs, % control |
|---|---|
| Example 2 | 85 |
| Example 3 | 39 |
| Example 4 | 96 |
| Example 5 | 0 |
| Example 6 | 0 |

The foregoing examples illustrate the acarid ovicidal activity of the compounds of the present invention. The compounds of Examples 5 and 6 show the lack of activity of the compounds when one of R or $R^1$ is an isopropyl group (Example 6), or when trichloromethylthio is the substituent at the nitrogen position rather than tetrachloroethylthio (Example 5).

As indicated above, the compounds of this invention have ideal mite ovicidal activity. Thus, the compounds are useful in preventing the development of damaging populations of mites or in causing the gradual reduction of existing populations. Mite eggs do not hatch to produce living young if these eggs have been treated with one of these compounds. The active compounds may be applied directly to the host containing the mite eggs, or to the environment wherein the mite eggs may be subsequently deposited. Thus, e.g., the compounds may be applied to living plants, such as fruit-bearing trees, vegetable crops, grain seed crops, hay crops, etc. Generally from 0.01 to 100 kilograms of compound per 10,000 $m^2$ of foilage may be used. It is, of course, recognized that the amount will depend upon the type of mite to be controlled, the weather conditions, the type of crop, the stage of development of the crop, the interval between applications, and the particular compound.

The compounds of this invention will generally be mixed with biologically inert liquids or solids of about 0.5 to 95 weight percent. Higher or lower amounts, of course, can be used to advantage. Preferably from 1 to 50 weight percent of the composition will be the compounds of this invention. Typical of the liquid carriers which may be admixed with the compounds of this invention include, in addition to acetone, such liquids as water, kerosene, xylene, alcohols, alkylated naphthylene and glycols. Typical solids which may be incorporated with the compounds include the natural clays, such as kaolin clays, diatomaceous earth, synthetic fine silica, talc, pyrophillite, etc.

The pesticidal formulations of the compounds of this invention may also contain stabilizers, spreading agents, sticking agents, fillers, other compatible pesticides, and the like.

As will be evident to those skilled in the art, various modifications of the invention can be made or followed in light of the foregoing disclosure and discussion without departing from the spirit or scope of the disclosure or from the scope of the following claims.

What is claimed is:

1. A compound of the formula

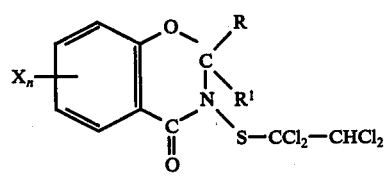

wherein X is fluorine, chlorine or bromine, or alkyl of 1 to 3 carbon atoms, $n$ is 0, 1 or 2, and R and $R^1$ are individually hydrogen, methyl or ethyl.

2. The compound of claim 1 wherein X is chlorine or methyl and $n$ is 0 or 1.

3. The compound of claim 2 wherein X is chlorine.

4. The compound of claim 1 wherein $n$ is 0.

5. 2-Methyl-3-(1′,1′,2′,2′-tetrachloroethylthio)-1,3-benzoxazin-4-one.

6. An ovicidal composition comprising an ovicidally effective amount of the compound of claim 1 and an inert pesticide carrier.

7. A method of killing acarid ova comprising applying to said ova an ovicidal amount of the compound of claim 1.

* * * * *